United States Patent [19]

Moeller et al.

[11] Patent Number: 5,231,024

[45] Date of Patent: Jul. 27, 1993

[54] MONOCLONAL ANTIBODIES AGAINST HUMAN TUMOR NECROSIS FACTOR (TNF), AND USE THEREOF

[75] Inventors: Achim Moeller, Limburgerhof; Franz Emling, Ludwigshafen, both of Fed. Rep. of Germany

[73] Assignee: BASF Aktiengesellschaft, Ludwigshafen, Fed. Rep. of Germany

[21] Appl. No.: 94,289

[22] Filed: Sep. 8, 1987

[30] Foreign Application Priority Data

Sep. 13, 1986 [DE] Fed. Rep. of Germany ....... 3631229

[51] Int. Cl.$^5$ .................. C12N 5/20; C12N 15/02; C07K 15/28; C12P 21/08
[52] U.S. Cl. .................. 435/240.27; 435/70.21; 435/172.2; 530/388.23
[58] Field of Search .................. 530/387, 388.23; 435/240.27, 70.21, 172.2, 548; 424/85.8

[56] References Cited

FOREIGN PATENT DOCUMENTS 186833 12/1985 European Pat. Off.
0218868 8/1986 European Pat. Off.

OTHER PUBLICATIONS.

Waldman Science 252: 1657–1662, 1991.
Pennica et al. PNAS 82: 6060, 1985.
Campbell, "Monoclonal Antibody Technology", Elsevier Press, 1984, p. 298.
Gamble et al PNAS 82: 8667, 1985.
Aggarwal et al. J. Biol. Chem. 260: 2345, 1985.
Wang et al. Science 228: 149, 1985.
Pennica et al. Nature 312: 724, 1984.
Beutler et al. Science 229: 869, 1985.
Urban et al. PNAS 83: 5233, 1986.
Hahn et al. PNAS 82: 3814 1985.
Kipps et al. pp. 108.1–108.9 in Weir et al. Handbook of Expt'l Immunol., vol. 4, Blackwell Sci Publ 1986.
Milstein pp. 107.1–107.12 in Weir et al., Eps. Handbook of Expt'l. Immunol., vol. 4, Blackwell Sci Publ 1986.
Sato et al. Proc. Japan Acad. 61 Ser. B: 471 1985.
Hayashi et al. In: Ishigami, ed. "Recent Adv. In Chemother. Proc. Int'l. Congr. Chemother, 14th vol., Anticancer Sect 2": 820, Univ. Tokyo Press, 1985.
Bringman et al. Hybridoma 4(1): 85 1985.
Liang et al. Biochem Biophys. Res Comm 137: 847 1986.
Koehler et al, Nature, vol. 256, pp. 495–497 (1975).
Moeller et al, Cytokine, vol. 2, pp. 162–169 (1990).
Chemical Abstract, vol. 104, No. 11, Mar. 1986, p. 534 No. 86989e.
Chemical Abstract, vol. 104, No. 9, Mar. 1986, p. 562 No. 67346b.
Chemical Abstract, vol. 105, No. 25, Dec. 1986, p. 612, No. 224436w.
Chemical Abstract, vol. 105, No. 23, Dec. 1986, p. 451 No. 207220d.
Chemical Abstract, vol. 105, No. 5, Aug. 1986, p. 579 No. 40912s.
Recent Adv. Chemother. Proc. Int. Congr. Chemoth, Chemoth. 14th 1985, pp. 820–821.
Hybridoma, vol. 6(5), pp. 489–507 (1987).
Nature, 1987, vol. 330, pp. 662–664.
Perlmutter et al., 1978, J. Immunol., vol. 121(2), pp. 568–572.
Spertini et al., 1989, Eur. J. Immunol., vol. 19, pp. 273–278.
Greenspan et al., 1987, J. Immunol., vol. 138(1), pp. 285–292.

Primary Examiner—David L. Lacey
Assistant Examiner—Paula Hutzell
Attorney, Agent, or Firm—Oblon, Spivak, McClelland, Maier & Neustadt

[57] ABSTRACT

New hybridoma cell lines which synthesize highly specific monoclonal antibodies (mAb) against human tumor necrosis factor (TNF), monoclonal antibodies against TNF, a process for the preparation of such hybridoma cell lines and antibodies, and the use of the monoclonal antibodies are described.

2 Claims, 1 Drawing Sheet

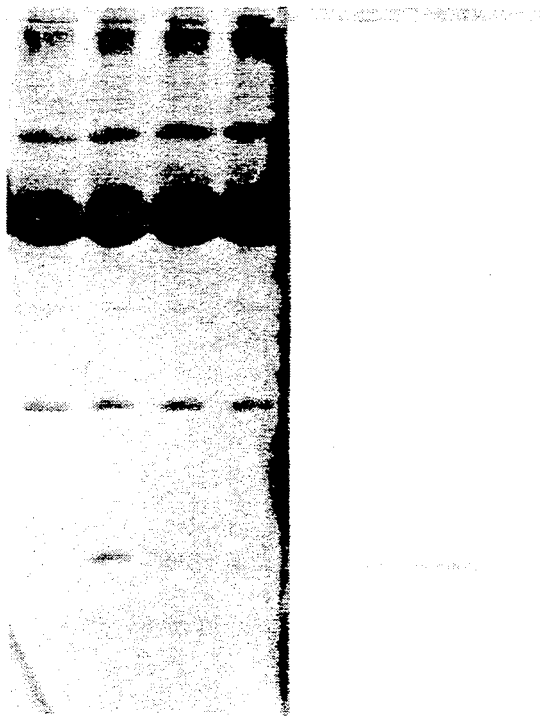

MONOCLONAL ANTIBODIES AGAINST HUMAN TUMOR NECROSIS FACTOR (TNF), AND USE THEREOF

The invention relates to hybridoma cell lines which synthesize highly specific monoclonal antibodies (mAb) against TNF, to monoclonal antibodies against TNF, to a process for the preparation of such hybridoma cell lines and antibodies, and the use of the monoclonal antibodies.

The fusion of mouse myeloma cells with spleen cells from immunized mice (Kohler and Milstein, Nature 256 (1975), 495–497) was the first indication that it is possible to obtain continuous cell lines which produce homogeneous (monoclonal) antibodies. Since then, numerous attempts have been made to prepare various hybrid cells (called hybridomas) and to use the antibodies which they produce for a variety of scientific investigations (see Current Topics in Microbiology and Immunology Vol. 81: Lymophocyte Hybridomas, Springer Verlag 1978).

Owing to its biological properties, TNF appears to be an interesting and promising agent for the treatment of oncoses. Detailed investigations were initially unsuccessful due to the extremely low concentration of TNF in natural cells. Not until gene manipulation developed, with the possibility of cloning human protein in lower organisms, did it become possible to express TNF in microorganisms. In highly purified form, this recombinant TNF (rTNF) has the same effects as natural TNF (nTNF).

Scientific investigations, as well as therapeutic use, have led to the need to detect not only the activity of TNF but also the protein TNF itself. The determination of biological activity is always laborious and costly.

The present invention relates to new monoclonal mouse antibodies against human, natural and recombinant, TNF, to the hybrid cell lines which produce them, to a process for their preparation, and to the use thereof.

The preparation of the monoclonal antibodies was based on known methods (Monoclonal Antibodies, Kennet et al., Plenum Press 1980, 363–419).

BALB/c mice were immunized by repeated injection of a small amount of the purified recombinant TNF from *E. coli*. As soon as sufficient antibodies were detectable in the serum, the spleen cells of these animals were fused with myeloma cells, and the hybrids were cultivated.

The individual cultures were subjected to a screening test for their content of specific antibodies against TNF.

Colonies derived from single cells of suitable hybridomas were isolated by the limiting dilution cloning method. Four hybrid cell lines were obtained in this way and were distinguished by their secreting monoclonal antibodies with different properties, namely the hybrid cell lines AM-1, AM-114, AM-195 and AM-199. These cell lines were deposited on May 8, 1987 at the European Collection of Animal Cell Cultures (ECACC), PHLS Centre for Applied Microbiology and Research, Porton Down, Salisbury SP4 OJ6 in Great Britain under the numbers 87 050801, 87 050802, 87 050803 and 87 050804.

These hybrid cells were grown by cultivation both in vitro and in vivo. The high growth rate in vivo made this method of culturing particularly suitable. It entailed BALB/c mice which had been pretreated with Pristan ® being given intraperitoneal injections of cells of the individual hybrid strains. The ascitic tumor which formed was harvested after about 8 to 10 days.

The monoclonal antibodies against TNF were isolated by working up either the supernatants of the in vitro cell culture or the ascitic fluid. The purification was based on the method of Bruch et al. (J. Immunol. Methods Vol. 53, 1982, 313–319).

The molecular properties of the antibodies were characterized as follows:

The molecular weight of the purified antibodies is greater than or equal to 150,000 daltons (determination by polyacrylamide gel electrophoresis).

The antibodies AM-1, AM-114 and AM-199 are of the IgG1 type, in which the heavy chain is gamma 1. The antibody AM-195 is of the IgG3 type, in which the heavy chain is gamma 3. The light chain is kappa in all the antibodies (determination by subtype-specific antibodies in an ELISA).

The monoclonal antibodies have a high affinity constant for TNF, of the order of $>10^9$ l/mol, and do not cross-react with lymphotoxin.

The relative positions of the binding sites for the individual antibodies on the TNF molecule were investigated by competitive binding of the antibodies.

TNF was immobilized on a microtiter plate. One biotin-labeled antibody was incubated with other, unlabeled, antibodies. The combinations with which there were antibody interactions for similar binding sites on TNF were investigated. The epitope to which the antibody AM-195 binds differs from that for AM-1 and AM-199. Slight competition was observed with AM-114.

The TNF activity was determined in a conventional cytotoxic assay. Recombinant and natural TNF were incubated with an excess of antibodies. The cytotoxic activity of both TNF preparations was neutralized by the antibody AM-195. The neutralization with AM-114 was one 10th as strong. This finding may be explained by assuming that different regions on the antigen react differently with the various antibodies: only the AM-195 monoclonal antibody reacts with a region responsible for biological activity.

The results on antibody binding and TNF neutralization reveal that at least three different epitopes of TNF can be recognized and defined by the collection of monoclonal antibodies.

Two designs of assay are possible in principle for the detection of a particular antigen using antibodies. In both it is necessary, if there is no natural marker in the antigen, to label one of the components. Either this is applied to the antigen, e.g. by a radioactive marker isotope, in which case a competitive displacement assay is normally used, such as the known radioimmunoassay (RIA), or the antibody is labeled, in which case the preferred type of assay is an immunoradiometric assay (IRMA), an enzyme-linked immunosorbent assay (ELISA) or a chemilumin-escence assay. Details of these various assay methods and variants thereof are known to those skilled in the art.

Another option is the coupling to the antibodies of low molecular weight haptens, which in turn can be detected specifically by a second reaction. An example of one which is commonly used is biotin reacting with streptavidin. All the antibodies according to the invention were therefore labeled with long-chain biotin and, in a subsequent step, visualized using streptavidin/horse radish peroxidase complex.

The assay which is described here is a solid-phase sandwich ELISA. An unlabeled antibody (AM-1 or AM-199) was bound, by passive adsorption or covalently, to a surface, e.g. microtiter plates, and the surface was blocked against non-specific binding in a known manner. TNF-containing samples and a biotin-labeled antibody (AM-195) were pipetted into the wells and incubated. It was shown that it is possible to detect TNF in samples with a detection limit of 10 pg/ml. rTNF has a specific activity of $8.0 \times 10^6$ U/mg in the mouse L929 assay, so that it is possible with this ELISA to detect 0.1 U TNF/ml. It was shown by Western blotting that the antibodies do not cross-react with any component of human serum. The antibodies according to the invention can thus be used for the determination of TNF in the serum of patients treated with TNF. They can also be used for current diagnostic purposes, e.g. to check the TNF level in serum and plasma.

Since the antibodies according to the invention inactivate TNF (see Example 6), they can be used for the treatment of diseases in which the TNF concentration in the blood is raised, such as septic shock. In addition, treatment with TNF antibodies may be indicated in the following disorders: transplant rejection, allergies, autoimmune diseases, rheumatic disorders, shock lung, inflammatory bone disorders, coagulation disturbances, and burns. The antibodies which are particularly suitable for this purpose are those which neutralize the cytotoxic activity of TNF.

It is also possible to use immunoaffinity chromatography to extract TNF from biological material containing it. This entails the antibodies being bound by known methods to a gel matrix, over which the TNF-containing solution is passed.

BRIEF DESCRIPTION OF THE FIGURE

The FIGURE SDS-PAGE analysis of human serum containing TNF and immunoblotting of human serum protein containing TNF bound to nitrocellulose using Mab HM-195.

The examples which follow are intended to illustrate the invention in detail:

EXAMPLE 1

Preparation of the Monoclonal Antibodies a) Immunization of BALB/c Mice

Female BALB/c mice were immunized intraperitoneally (i.p.) with 30 μg of rTNF in 0.5 ml of complete Freund's adjuvant. 14 days later the animals again received 30 μg of the antigen intraperitoneally in incomplete Freund's adjuvant. Two further intraperitoneal immunizations, each with 30 μg of antigen, were carried out at intervals of 14 days. Three days after the last dose of antigen the spleens of 2 animals were removed.

b) Preparation of a Spleen Cell Suspension

A cell suspension was prepared from the removed spleens by forcing the organs through a stainless steel screen (pore width 100 μm). The cells were transferred into Dulbecco's minimal essential medium (DMEM) which was supplemented with 4.5 g/l glucose, 10 mM glutamine, 1,000 units/ml penicillin, 100 μg/ml streptomycin and 15% fetal calf serum. The cells were washed three times with medium and then resuspended at the desired concentration in the same medium. In general, about 5 to $10 \times 10^7$ cells were obtained from each spleen.

c) Growth of the Myeloma Cells

The myeloma cells Sp2/0-Ag14 (ATCC No. CRL 8287) were used for fusion. The cells are resistant to 20 μg/ml 8-azaguanine but are no longer able to grow in a medium containing hypoxanthine, aminopterin and thymidine (HAT). They were cultivated in DMEM which was supplemented with 4.5 g/l glucose, 10 mM glutamine, 1,000 units/ml penicillin, 100 μg/ml streptomycin and 15% fetal calf serum (complete medium). The cells were used in the logarithmic phase of growth for fusion.

d) Cell Fusion

The spleen cell suspensions were mixed with the myeloma cells in the ratio 5:1 and washed with serum-free DMEM. The washed cells were resuspended in 30 ml of serum-free DMEM and centrifuged in a 50 ml conical polypropylene tube at 800 rpm for 5 minutes. The supernatant was quantitatively aspirated. Very carefully, 0.5 ml of a 50% solution of polyethylene glycol (PEG, Boehringer) of molecular weight 2,000 was added to the pellet, which was gently tapped to mix it with the PEG, and the mixture was then centrifuged at 1,000 rpm for three minutes. 10 ml of DMEM were then added, and the cell pellet was carefully suspended and then centrifuged down at 2,000 rpm for three minutes. The cell pellet was resuspended at a concentration of $2 \times 10^6$ cells/ml in HAT medium, and 0.2 ml portions were distributed on microtiter plates. On the preceding day, about 50,000 peritoneal mononuclear cells, mainly macrophages, had been placed in the wells as feeder cells.

e) Selecting and Culturing of the Hybridomas

After the cell fusion, the cells were cultivated in Littlefield HAT medium (Science, Vol. 145, 1964, 709–712) at 37° C. in a moist atmosphere containing 5% $CO_2$. The cultures were fed twice a week by replacing half the medium by fresh HAT medium. After some weeks, supernatants from hybridoma cell cultures were examined for the presence of anti-human tumor necrosis factor activity. The hybridomas which had positive results in the screening test were selected for cloning. This entailed the hybridomas being subjected to a limiting dilution technique, in which an average of 0.5 cells/-well was placed in each of 96 microtiter wells, and $10^5$ mouse thymocytes were added as feeder cells. The antibody-producing cells selected by this cloning procedure were multiplied, frozen and stored in liquid nitrogen in complete medium containing 10% fetal calf serum and 10% dimethyl sulfoxide.

f) Screening Test for TNF-specific Antibodies rTNF was diluted to 3 μg/ml in PBS (phosphate-buffered saline, composed of 0.8% NaCl and 0.02 molar sodium phosphate, adjusted to pH 7.4 with HCl or NaOH). 0.1 ml portions of this solution were placed in wells of Microtiter ® plates. After two hours at room temperature, the supernatant was aspirated, and the wells were treated with 0.3 ml of a 1% bovine serum albumin solution (Sigma, RIA grade) for not less than 30 minutes. The supernatant was then discarded. Supernatants from growing hybridoma cell lines, which were approximately 20–30% confluent, or dilutions of sera from immunized mice were incubated at room temperature for not less than two hours. The wells were washed several times with 0.3 ml of PBS. Then incubation was carried out with 0.1 ml of a suitable concentration of anti-mouse immunoglobulin antibodies (Miles) for two hours at room temperature. These antibodies were coupled to peroxidase as enzyme marker. Wells with a positive peroxidase reaction indicated antigen-specific antibodies.

Cell growth was observed in 80% of 360 wells which were originally used. 12 of these had positive results in the TNF screening test. On repeat testing, 11 of these were positive. Four different monoclonal hybridomas were followed up for the present invention: AM-1, AM-195, AM-114 and AM-199.

g) Expansion of Hybridoma Cell Cultures

Expansion in the cell culture (in vitro): About $2 \times 10^7$ cells were introduced into cell-culture bottles with a growth area of 175 cm$^2$. After three days, the cell-free supernatant contained in the region of 10 to 20 µg/ml monoclonal antibodies secreted by the cells. Expansion in ascitic mice (in vivo):

BALB/c mice received 0.5 ml i.p. Pristan ® for conditioning of the peritoneum. A suspension of 5 to $10 \times 10^6$ hybridomas in PBS was administered i.p. to each of the pretreated animals within a period of 1 to 2 weeks. After 8 to 10 days, the peritoneum was pierced with a needle, and the cell-containing ascitic fluid was collected.

The cellular constituents of the samples of ascitic fluid were removed by centrifugation (5,000 rpm, 5 minutes). The supernatant, which contained the monoclonal antibodies, was frozen in aliquots at −70° C., or was purified by chromatography to at least 90%, as assessed by sodium dodecyl sulfate polyacrylamide gel electrophoresis (German Laid-Open Application DOS 3,330,160).

h) Typing of the Monoclonal Antibodies

The monoclonal antibodies were characterized in an ELISA system. The wells of a microtiter plate were charged with rTNF (5 µg/ml). After the plate which had been prepared in this way had been incubated, at room temperature for 2 hours, with purified monoclonal antibodies from a cell culture, a second incubation step (room temperature for 2 hours) was carried out with anti-mouse immunoglobulins of various classes and subclasses and with various classes of light and heavy immunoglobulin chains (Miles). In another step, a peroxidase-labeled goat anti-rabbit immunoglobulin (Miles) was added. After incubation for one hour, the enzyme reaction was started by addition of the staining substrate tetramethylbenzidine (Miles) and hydrogen peroxide. The results are compiled in Table 1.

TABLE 1

| Name of antibody | Class | Chain Heavy | Light |
|---|---|---|---|
| AM-1 | IgG | gamma 1 | kappa |
| AM-114 | IgG | gamma 1 | kappa |
| AM-195 | IgG | gamma 3 | kappa |
| AM-199 | IgG | gamma 1 | kappa | i) Labeling of the Monoclonal Antibodies

NHS-LC-Biotin (Pierce) was dissolved in PBS and adjusted to a concentration of 1 mg/ml. 0.1 ml of this solution was mixed with 0.1 ml of purified monoclonal antibodies (0.5 mg/ml PBS), and the solution was incubated at room temperature for two hours. Following the reaction, the solution was made up to 1 ml with PBS and dialyzed against PBS at 4° C. The dialysate, that is to say the solution in the dialysis tube, was stored at 4° C. until used.

EXAMPLE 2

Affinity of the Monoclonal Antibodies for TNF

The affinity constants were determined using data from an ELISA. This entailed the purified antibodies being titrated against a constant amount of TNF, and the binding of the antibodies being detected by binding of peroxidase-labeled rabbit anti-mouse immunoglobulin. The binding data were analyzed using a specific program.

TABLE 2

| Affinity constants of the monoclonal antibodies | |
|---|---|
| Name of antibody | $K_a \times 10^9 \: 1 \times mol^{-1}$ |
| AM-1 | 1.5 ± 30% |
| AM-114 | 1.4 ± 30% |
| AM-195 | 3.5 ± 30% |
| AM-199 | 2.0 ± 30% |

The association constants $K_a$ demonstrate the high affinity of the anti-TNF antibodies.

EXAMPLE 3

Neutralization of the Cytotoxic Activity of TNF

The biological activity of TNF in vitro was determined by lysis of the mouse cell line L929 (ATCC No. CCL1) as described by Aggarwal et al. (J. Biol. Chem. Vol. 260, 1985, 2345-2354). The concentration of TNF chosen in tests of the neutralization of the cytotoxic activity of TNF by the monoclonal antibodies was that at which at least 90% of the cells lysed. The antibodies were diluted in complete medium in 1:2 steps in microtiter plates. 0.05 ml of recombinant or natural TNF (1.3 ng/ml) was added to each antibody solution (0.1 ml), and the mixture was incubated at room temperature for two hours. Then 50,000 L929 cells in 0.05 ml of medium were added and, after incubation in an incubator for 20 to 24 hours, the cells were fixed and stained with crystal violet.

The cytotoxic effect of TNF leads to lysis of the cells, which are therefore washed away during staining. However, if sufficient antibody is present, the cytotoxic effect of TNF is neutralized and the cells are stained.

TABLE 3

| Neutralization of the cytotoxic activity of TNF | |
|---|---|
| mAb | Neutralization |
| AM-1 | − |
| AM-114 | + |
| AM-195 | ++ |
| AM-199 | − |

As can be seen from Table 3, three different classes of antibodies were found in the neutralization test. Neutralization of TNF was found at a monoclonal antibody concentration of 0.2 µg/ml AM-195, and 2 µg/ml AM-114, while neutralization was incomplete with 20 µg/ml AM-1 and AM-199.

The determination of the association constants in Example 2 showed that the antibodies bind TNF approximately to the same extent. Categorization of the antibodies into those which neutralize strongly, weakly or not at all provides information allowing various epitopes on the TNF molecule to be distinguished. The results on the antibody binding and TNF neutralization reveal that at least three different epitopes of TNF can be recognized and defined by the collection of monoclonal antibodies.

EXAMPLE 4

Determination of TNF a) Selection of a Suitable Pair of Monoclonal Antibodies

To distinguish between competitive binding of two antibodies to the same epitope and additive binding to different epitopes, the binding to immobilized TNF was tested with the antibodies alone and in all the possible pairwise combinations. TNF was bound as described in Example 1. Purified antibodies were diluted in steps of 1:4, starting with 24,000 ng/ml. Then biotinylated antibody AM-195 was added, followed by incubation for 90 minutes. The wells were washed with PBS/0.05% Tween ® 20, and streptavidin-peroxidase complex (BRL) was added and the mixture was incubated for 30 minutes. After a washing step, 0.1 ml of peroxidase substrate (see Example 4 b) was added to each well. Competitive binding results in quenching of the signal. As is evident from Table 4, the TNF epitope which binds the monoclonal antibody AM-195 differs from that for AM-1 or AM-199. There is slight competition with AM-114. For this reason, the subsequent experiments were carried out with immobilized AM-1 or AM-199 antibodies and biotin-labeled AM-195.

TABLE 4

Effect of mAb on the binding of biotin-labeled AM-195 to TNF

| µg mAb/ml | % Binding | | | |
| --- | --- | --- | --- | --- |
| | 195 | 114 | 199 | 1 |
| 24000 | 3 | 33 | 100 | 100 |
| 6000 | 4 | 85 | 100 | 100 |
| 1500 | 16 | 100 | 100 | 100 |
| 375 | 63 | 100 | 100 | 100 |
| 62 | 95 | 100 | 100 | 100 |
| 0 | 100 | 100 | 100 | 100 | b) Design of Enzyme Immunoassay

The antibody AM-1 or AM-199 was immobilized by passive adsorption or covalent bonding on a carrier (beads, filter, polystyrene or polyvinyl chloride microtiter plate, filter paper or other materials). The specificity of monoclonal antibodies permits only the specific antigen, in this case TNF, to be bound via a single molecular binding site on the antigen The amount of TNF which can be bound is proportional to the concentration and amount of the antigen in solution. The antigen is recognized by binding the antibody AM-195 to another molecular binding site. The antibody AM-195 carries a signal. The amount of the immobilized signal is thus directly proportional to the amount of immobilized antigen, and thus also to the concentration of the antigen in the solution under investigation.

Assay Procedure

1. Coating

Purified antibodies AM-1 or AM-199 were diluted in adhesion buffer (sodium bicarbonate buffer, pH 9.5, 4.2 g/l=0.05M) to 5 µg/ml. The wells of a microtiter plate were incubated with 0.1 ml of this solution at 4° C. for 16 to 20 hours.

2. Blocking

The solution obtained in 1 was aspirated, and the wells were washed twice with PBS (2 g/l NaCl, 0.2 g/l KCl, 1.44 g/l $Na_2HPO_4 \times 2H_2O$, 0.2 g/l $KH_2PO_4$, pH 7.0). They were then blocked with 1% bovine serum albumin solution (Sigma, RIA grade) at room temperature for 30 minutes.

3. Serial Dilutions and TNF Samples

The solution from Example 2 was aspirated, and the wells were washed twice with PBS. rTNF was adjusted to 2.5 ng/ml, and diluted in 1:2 steps, with buffer I (1 g of bovine serum albumin, Sigma RIA grade, added to 1 l of PBS). 0.1 ml samples were pipetted into each well and incubated at room temperature for 2-4 hours. After washing 3 times with buffer (washing buffer: PBS+0.1% Tween ® 20), 0.1 ml of biotin-labeled antibody AM-195 was added. The conjugate prepared by the method in Example 1 h) was diluted 1:400 with buffer I and incubated at room temperature for 2 hours or at 4°-10° C. for 16-20 hours.

4. Amplification System

The wells were washed 3 times with washing buffer and then incubated with 0.1 ml of streptavidin-peroxidase complex (BRL, diluted 1:2,000 in PBS/BSA buffer) at room temperature for 30 min.

5. Development

The wells were washed 3 times with washing buffer, and 0.1 ml of peroxidase substrate was pipetted into each well, and incubation was carried out at room temperature for 30 minutes. The reaction was stopped with 0.1 ml of 2M $H_2SO_4$ per well. The absorption in the microtiter plate at a wavelength of 450 nm was recorded within one hour. A characteristic calibration curve is shown in FIG. 1. The detection limit for TNF is 10 pg/ml.

Peroxidase Substrate

TMB solution: 42 mM TMB (3,3',5,5'-tetramethylbenzidine, Miles) in DMSO.

Substrate buffer: 50 g of sodium acetate added to 1 l of water, and pH adjusted to 4.9 with 1 g of citric acid. 0.1 ml of the TMB solution is slowly added, with shaking, to 10 ml of substrate buffer, followed by 1.47 µl of 30% $H_2O_2$ (extra pure, Merck).

c) Determination of TNF in Human Serum

Recombinant and/or natural TNF was adjusted to 2.5 ng/ml in buffer I (Example 4 b) or in human serum, and was diluted in 1:2 steps under the same conditions. 0.1 ml was pipetted into each of the wells which had been previously been coated with antibody AM-199 or AM-1, as described in Example 4 b). The subsequent procedure is described in Example 4 b).

As is evident from the FIGURE, none of the components of human serum interferes with the determination of TNF using monoclonal antibodies.

d) Cross-reaction of the Antibodies with Lymphotoxin

Possible cross-reaction of the antibodies with lymphotoxin was tested as in Example 1e, with the wells of the microtiter plate being coated with purified recombinant lymphotoxin. No binding of the antibodies AM-1, AM-114, AM-195 or AM-199 to lymphotoxin was found.

EXAMPLE 5

Detection of TNF in Serum by Western Blotting Using Monoclonal Antibodies

Human serum to which various amounts of TNF had been added was fractionated by gel electrophoresis in a 12.5% gel by the method of Laemmli (J. Mol. Biol., Vol. 80, 1973, 575–599). The Western blotting method was that described by Burnett, W. N. (Anal. Biochem., Vol. 112, 1981, 195–203) and Reines, D. et al. (J. Biol. Chem., Vol. 260, 1985, 1133–1139). The proteins on the gel were blotted onto a nitrocellulose membrane (Schleicher and Schüll) overnight. The nitrocellulose membrane was incubated with 1% gelatin solution (Bio-Rad, 10 g of gelatin being added to 1 l of PBS) at room temperature for three hours. The nitro-cellulose membrane was then incubated at room temperature for two hours with 20 ml of antibody solution which had been diluted to 1 $\mu$g/ml in buffer (0.1% gelatin in PBS). The supernatant was decanted off, and the membrane was washed several times. TNF was visualized on the nitrocellulose membrane using peroxidase-labeled anti-mouse immunoglobulin. The detection limit is 30 ng of TNF. As is evident from the FIGURE, the monoclonal antibody AM-195 does not react with any component in human serum and can thus be regarded as specific for TNF. The results were the same for the antibodies AM-1, AM-114 and AM-199.

EXAMPLE 6

Neutralization of TNF

The protective effect of the mAb against TNF was investigated under in vivo conditions in male BALB/c (Tests 1, 2 and 4) and C3H/HeN (Test 3) mice. Mice which were 4–6 weeks old were randomized and divided into groups of 3 or 5 animals. The substances were administered intravenously into the lateral caudal vein (volume administered 10 ml/kg). Before the injection, TNF was dissolved in buffer A (150 mM NaCl and 0.18% bovine serum albumin (Sigma, RIA grade) and stored at 4°–10° C. for 6 hours. The toxicity of TNF was at a maximum after this time. TNF was added first, followed by the mAb 15–30 minutes later. The mortality rates were determined after 24 hours. Table 5 shows the results (3/5 means that 3 of 5 animals died).

TABLE 5

| Substances administered | Test No. | | | |
|---|---|---|---|---|
| | 1 | 2 | 3 | 4 |
| Buffer A | 0/3 | 0/5 | 0/5 | 0/5 |
| mAb 10 mg/kg | 0/3 | 0/5 | 0/5 | 0/5 |
| mAb 5 mg/kg | 0/3 | 0/5 | 0/5 | 0/5 |
| TNF 1 mg/kg | 3/3 | 0/5 | 4/5 | 4/5 |
| TNF 1 mg/kg + mAb 1 mg/kg | 1/3 | 2/5 | 1/5 | 3/5 |
| TNF 1 mg/kg + mAb 5 mg/kg | 0/3 | 0/5 | 0/5 | 0/5 |
| TNF 2 mg/kg | 3/3 | 5/5 | 1/5 | 4/5 |
| TNF 2 mg/kg + mAb 2 mg/kg | 3/3 | 4/5 | 2/5 | 5/5 |
| TNF 2 mg/kg + mAb 10 mg/kg | 0/3 | 0/0 | 0/5 | 0/5 |

As can be seen in Table 5, the neutralizing antibody AM-195 is able to neutralize a lethal dose of TNF in the mouse. The survival rates of the animals depend on the ratio between the weights of antibody and TNF. Complete abolition of TNF toxicity is found at a ratio of 5:1. Assuming that TNF is a trimer (FEBS Lett. 211, (1987) 179), this corresponds to a molar ratio of antibody to TNF of 1.6 to 1.

In the mouse, TNF cannot be neutralized by nonneutralizing antibodies.

We claim:
1. The cell line ECACC 87 050801.
2. A MAb produced by the cell line of claim 1.

* * * * *